(12) United States Patent
Imperante et al.

(10) Patent No.: US 6,362,233 B1
(45) Date of Patent: Mar. 26, 2002

(54) METHOXY CAPPED ALKOXYLATED GLYCERIN COMPOUNDS

(75) Inventors: John Imperante, Somerville, NJ (US); Anthony J. O'Lenick, Jr., Dacula, GA (US)

(73) Assignee: Phoenix Research Corporation, Somerville, NJ (US)

(*) Notice: Subject to any disclaimer, the term of this patent is extended or adjusted under 35 U.S.C. 154(b) by 0 days.

(21) Appl. No.: 09/751,965

(22) Filed: Jan. 2, 2001

(51) Int. Cl.[7] .............................................. A61K 31/08
(52) U.S. Cl. ...................................... 514/723; 424/401
(58) Field of Search ........................... 424/401; 514/723

(56) References Cited

U.S. PATENT DOCUMENTS 4,046,914 A * 9/1977 Hallgren et al. ............ 514/723

OTHER PUBLICATIONS

Abstract of JP 2001107075 A; Abe et al, "Aqueous Working Fluid", Apr. 17, 2001.*

* cited by examiner

*Primary Examiner*—Michael G. Hartley
*Assistant Examiner*—Michael A. Willis

(57) ABSTRACT

The present invention is directed to a series of methoxy capped water-soluble emollient products that exhibit resistance to hydrolysis with water. The present invention also provides a process for treating skin, which comprises contacting the skin with an effective emollient amount of the compounds of the present invention.

9 Claims, No Drawings

METHOXY CAPPED ALKOXYLATED GLYCERIN COMPOUNDS

BACKGROUND OF THE INVENTION

The present invention is directed to a series of methoxy capped water-soluble emollient products that exhibit resistance to hydrolysis with water. The present invention also provides a process for treating skin, which comprises contacting the skin with an effective emollient amount of the compounds of the present invention.

Glycerin ethoxylates are per se poor emolients. This is thought to be related to the fact that hydroxyl groups make the molecule too polar to be substantive to the skin and provide conditioning effects. An approach that has met with limited success is the reaction of the hydroxyl group with acetic anhydride to produce an acetoxy-capped product. The difficulty is that the products produced using this technology have free acetic acid, which has a typical biting odor and therefore must be removed. In addition and more importantly the acetoxy-capped products have a limited pH range over which they are stable to hydrolysis. The hydrolysis process occurs at pH below 6 and cleaves off the acetoxy group giving the smelly acetic acid and the ineffective hydroxyl-containing product. Since the compounds used as skin emolients are generally delivered at a pH of around 5 (natural skin pH) the acetoxy capped materials hydrolyze and are unacceptable in products that are not used rapidly. Since most personal care compounds are not used instantly when produced, product instability is not acceptable. It was not until the compounds of the present invention which feature methoxy capped products that are stable to hydrolysis was it possible to make stable products containing water soluble emolients. Acetoxy capped products are esters having a —C(O)CH$_3$ group on the hydroxyl group. Methoxy groups are ethers and feature the hydrolytically stable —OCH$_3$ group.

THE INVENTION

Objective of the Invention

The present invention is directed to a series of methoxy capped water-soluble emollient products that exhibit resistance to hydrolysis with water. It is also an objective of the present invention to provide a process for treating skin which comprises contacting the skin with an effective emollient amount of the compounds of the present invention.

SUMMARY OF THE INVENTION

The present invention is directed to a series of methoxy capped water-soluble emollient products that exhibit resistance to hydrolysis with water. It is also an objective of the present invention to provide a process for treating skin, which comprises contacting the skin with an effective emollient amount of the compounds of the present invention.

DETAILED DESCRIPTION OF THE INVENTION

The compounds of the present invention conform to the following structure:

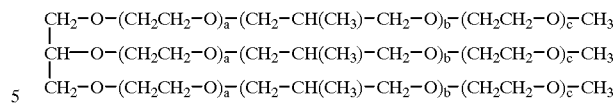

wherein:

a, b and c are independently integers ranging from 0 to 20 with the proviso that a +b+c be at least 1.

The present invention also comprises a process for treating skin which comprises contacting the skin with an effective emollient amount of compounds conforming to the following structure:

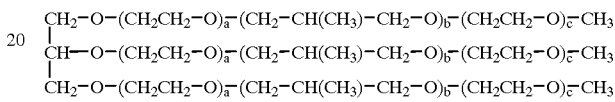

wherein:

a, b and c are independently integers ranging from 0 to 20 with the proviso that a +b+c be at least 1. The effective emollient concentration ranges from 0.1% to 25% by weight.

The compounds of the present invention are made by reacting an ethoxylated glycerin with methyl chloride as follows;

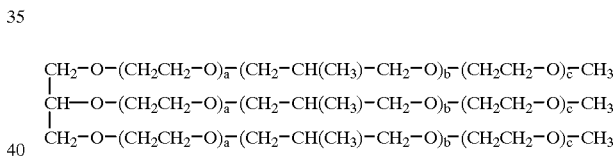

wherein:

a, b and c are independently integers ranging from 0 to 20 with the proviso that a +b+c be at least 1.

The present invention also comprises a process for treating skin, which comprises contacting the skin with an effective emollient amount of compounds conforming to the following structure;

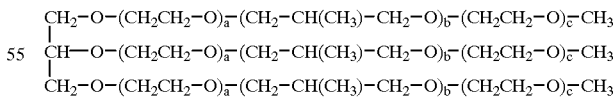

wherein.

a, b and c are independently integers ranging from 0 to 20 with the proviso that a +b +c be at least 1.

The present invention also comprises a process for treating skin, which comprises contacting the skin with an effective emollient amount of compounds conforming to the following structure,

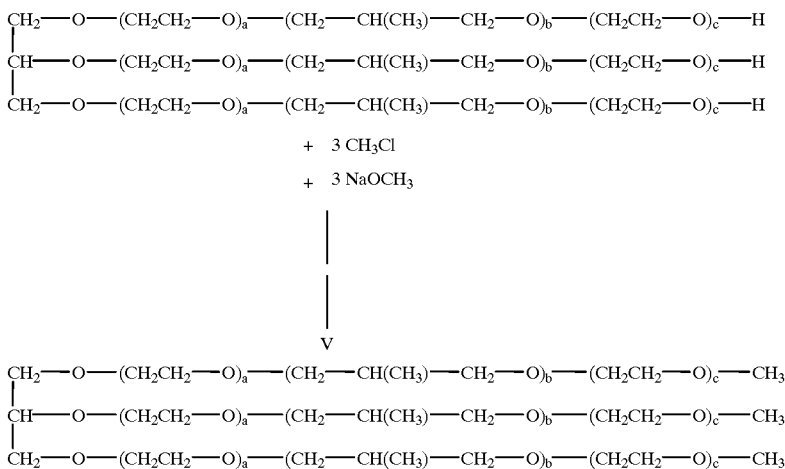

Preferred Embodiments

In the first set of preferred embodiments directed toward the methoxy capped glyceryl compound conforming to the following structure:

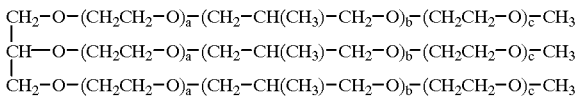

wherein:
In a preferred embodiment a is 1, b is 0 and c is 0.
In a preferred embodiment a is 1, b is 2 and c is 1.
In a preferred embodiment a is 7, b is 0 and c is 0.
In a preferred embodiment a is 20, b is 20 and c is 20.
In a preferred embodiment a is 10, b is 10 and c is 0.
In a preferred embodiment a is 0, b is 10 and c is 0.
In a preferred embodiment 1 wherein a is 10, b is 2 and c is 10.
In a preferred embodiment a is 2, b is 2 and c is 5.

In another set of preferred embodiments directed to a process for treating skin which comprises contacting the skin with an effective emollient amount of compounds conforming to the following structure;

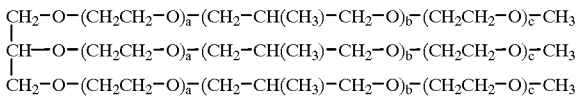

wherein;
a, b and c are independently integers ranging from 0 to 20 with the proviso that a +b+c be at least 1.

In a preferred embodiment the effective emollient concentration ranges from 0.1% to 25% by weight.
In a preferred embodiment of this set a is 1, b is 0 and c is 0.
In a preferred embodiment of this set a is 1, b is 2 and c is 1.
In a preferred embodiment of this set a is 7, b is 0 and c is 0.
In a preferred embodiment of this set a is 20, b is 20 and c is 20.
In a preferred embodiment of this set a is 10, b is 10 and c is 0.
In a preferred embodiment of this set a is 0, b is 10 and c is 0.
In a preferred embodiment of this set 1 wherein a is 10, b is 2 and c is 10.
In a preferred embodiment of this set a is 2. b is 2 and c is 5.

EXAMPLES

1. Alkoxylation of Glycerin

General Procedure

To 96.0 grams of glycerin is added 0. 1% by weight (based upon the total weight of the alkoxylate being prepared) of sodium methylate. Apply nitrogen sparge. Heat to 220–240 F. and apply vacuum for 30 minutes. Add the specified amount of ethylene oxide 1, slowly maintaining temperature at between 260– 290 F. and pressure at between 45 and 90 psig. After all the oxide has been added, hold 2 hrs then cool to ambient. Next, the specified amount of propylene oxide is added, followed in turn by the specified amount of ethylene oxide 2.

Example 1

To 96.0 grams of glycerin is added 0.1% by weight (based upon the total weight of the alkoxylate being prepared) of sodium metylate. Apply nitrogen sparge. Heat to 220–240 F. and apply vacuum for 30 minutes. Add 44 grams of ethylene oxide slowly maintaining temperature at between 260–290 F. and pressure at between 45 and 90 psig. After all the ethylene oxide #1 has been added, hold 2 hrs then cool to ambient. Next, add 0 grams of propylene oxide is added, followed in turn by the 0 grams of ethylene oxide #2, hold 2 hrs then cool to ambient.

Examples 2

Example 1 is repeated only this time the specified amount of the specified ethylene oxide and propylene is added replacing the specific quantities specified in example 1.

| | Ethylene Oxide 1 | | Propylene Oxide | | Ethylene Oxide 2 | |
|---|---|---|---|---|---|---|
| Example | Moles | Grams | Moles | Grams | Moles | Grams |
| 2 | 1 | 44 | 2 | 118 | 1 | 44 |
| 3 | 7 | 308 | 0 | 0 | 0 | 0 |

-continued

| | Ethylene Oxide 1 | | Propylene Oxide | | Ethylene Oxide 2 | |
|---|---|---|---|---|---|---|
| Example | Moles | Grams | Moles | Grams | Moles | Grams |
| 4 | 20 | 880 | 20 | 1180 | 20 | 880 |
| 5 | 10 | 440 | 10 | 590 | 0 | 0 |
| 6 | 0 | 0 | 10 | 590 | 0 | 0 |
| 7 | 10 | 440 | 2 | 118 | 10 | 440 |
| 8 | 2 | 88 | 2 | 118 | 5 | 220 |

2. Reaction with $CH_3Cl$
Procedure

To suitable vessel equipped with agitation is added 216.0 grams of 25% sodium methylate and the specified amount of the specified glycerin alkoxylate (examples 1–8). The reaction mass is sparged with nitrogen and vaccuum is applied. The vacuum is relieved and nitrogen is bubbled through the reaction mass.

Next the reaction mass is heated to 75–85 C. and the methyl chloride is added. The reaction progress is monitored by alkali value, which becomes vanishingly small as the reaction nears completion. Methanol is stripped off and sodium chloride filtered off before the product is used.

| | Glycerin Alkoxylate | |
|---|---|---|
| Example | Example | Grams |
| 9 | 1 | 76.0 |
| 10 | 2 | 238.0 |
| 11 | 3 | 340.0 |
| 12 | 4 | 2940.0 |
| 13 | 5 | 1502.0 |
| 14 | 6 | 622.0 |
| 15 | 7 | 1030.0 |
| 16 | 8 | 488.0 |

In preparing the compounds of the present invention it must be understood that one mole of NaCl and one mole of $CH_3OH$ are produced per mole of methyl chloride added. The NaCl is removed by filtration and the methanol is removed by applying vacuum and heating to 80 C.

APPLICATIONS EXAMPLES

The compounds of the present invention are stable to hydrolysis and provide emollient properties to skin. Typical of the stability of the compounds of the present invention compared to acetate salts is as follows:
Procedure
pH adjusted to 5 with lactic acid.
10% test material added to get solution.
Placed at 50 C. for 5 days.

| Material Tested | Result |
|---|---|
| Glycereth-7-acetate | Acetic smell, hydrolyzed |
| Glycereth-7-Methoxy capped | Stable clear liquid |

While the illustrative embodiments of the invention have been described with particularity it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

What is claimed is:

1. A methoxy capped glyceryl compound conforming to the following structure:

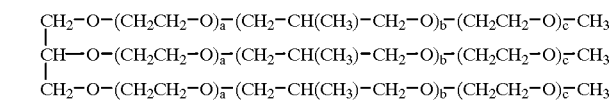

wherein;
  a, b and c are independently integers ranging from 0 to 20 with the proviso that a +b+c be at least 1.

2. A methoxy capped glyceryl compound of claim 1 wherein a is 1, b is 0 and c is 0.

3. A methoxy capped glyceryl compound of claim 1 wherein a is 1, b is 2 and c is 1.

4. A methoxy capped glyceryl compound of claim 1 wherein a is 7, b is 0 and c is 0.

5. A methoxy capped glyceryl compound of claim 1 wherein a is 20, b is 20 and c is 20.

6. A methoxy capped glyceryl compound of claim 1 wherein a is 10, b is 10 and c is 0.

7. A methoxy capped glyceryl compound of claim 1 wherein a is 0, b is 10 and c is 0.

8. A methoxy capped glyceryl compound of claim 1 wherein a is 10, b is 2 and c is 10.

9. A methoxy capped glyceryl compound of claim 1 wherein a is 2, b is 2 and c is 5.

* * * * *